(12) United States Patent
Jordan

(10) Patent No.: US 8,685,037 B1
(45) Date of Patent: *Apr. 1, 2014

(54) BONE REDUCTION AND PLATE CLAMP ASSEMBLY

(76) Inventor: Christopher Jordan, Midwest City, OK (US)

( * ) Notice: Subject to any disclaimer, the term of this patent is extended or adjusted under 35 U.S.C. 154(b) by 1037 days.

This patent is subject to a terminal disclaimer.

(21) Appl. No.: 12/798,163

(22) Filed: Mar. 30, 2010

Related U.S. Application Data

(63) Continuation-in-part of application No. 12/655,005, filed on Dec. 22, 2009, now Pat. No. 8,579,950.

(51) Int. Cl.
*A61B 17/58* (2006.01)

(52) U.S. Cl.
USPC .......................................... 606/105; 606/324

(58) Field of Classification Search
USPC ................ 606/54, 57, 86 R, 324, 55, 74, 105
See application file for complete search history.

(56) References Cited

U.S. PATENT DOCUMENTS

| | | | |
|---|---|---|---|
| 2,362,957 A | 11/1944 | Hackett | |
| 2,427,128 A | 9/1947 | Ettinger | |
| 3,477,429 A | 11/1969 | Sampson | |
| 4,187,840 A | 2/1980 | Watanabe | |
| 5,563,349 A | 10/1996 | Burke | |
| 5,797,919 A | 8/1998 | Brinson | |
| 6,238,414 B1 * | 5/2001 | Griffiths | 606/205 |
| 6,315,780 B1 * | 11/2001 | Lalonde | 606/86 R |
| 6,425,901 B1 * | 7/2002 | Zhu et al. | 606/142 |
| 6,605,088 B1 | 8/2003 | St. Onge | |
| 6,623,483 B1 | 9/2003 | Kazakov | |
| 6,921,404 B2 | 7/2005 | Bimman | |
| 8,192,449 B2 * | 6/2012 | Maier et al. | 606/151 |
| 8,231,623 B1 * | 7/2012 | Jordan | 606/54 |
| 2008/0009871 A1 | 1/2008 | Orbay | |
| 2008/0027471 A1 | 1/2008 | Hauri | |

* cited by examiner

*Primary Examiner* — Kevin T Truong
*Assistant Examiner* — Michael Araj
(74) *Attorney, Agent, or Firm* — Randal D. Homburg

(57) ABSTRACT

A pair of clamps are attached to a damaged linear or non-linear bone one each side of a fracture site during a surgical reduction, one clamp on each side of the fracture site, after which the two clamps are slidably engaged to a pivotal alignment bar, with the clamps then being adjusted to properly align the linear or non-linear bone for a surgical attachment using a bone plate. The pivotal alignment bar provides at least one pivotal ball joint which may be aligned as a straight bar for a linear bone or adjusted to an angle for non-linear bones to achieve optimal alignment of the bone. Each clamp provides axially adjustable plate retainers which slides along a track on the end of each segment of the each clamp to position the retainers at a location where the bone plate is to be attached to the bone.

14 Claims, 8 Drawing Sheets

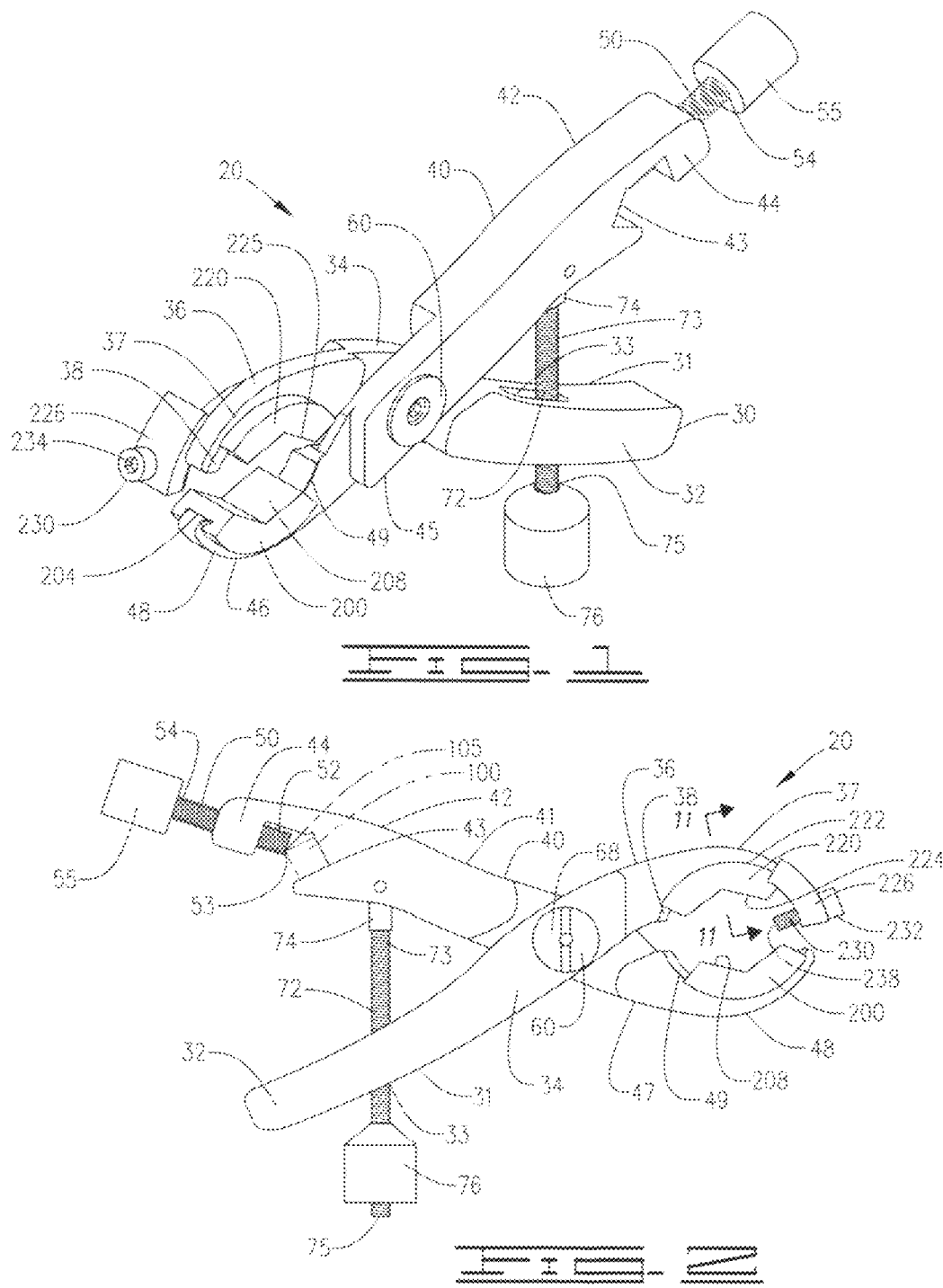

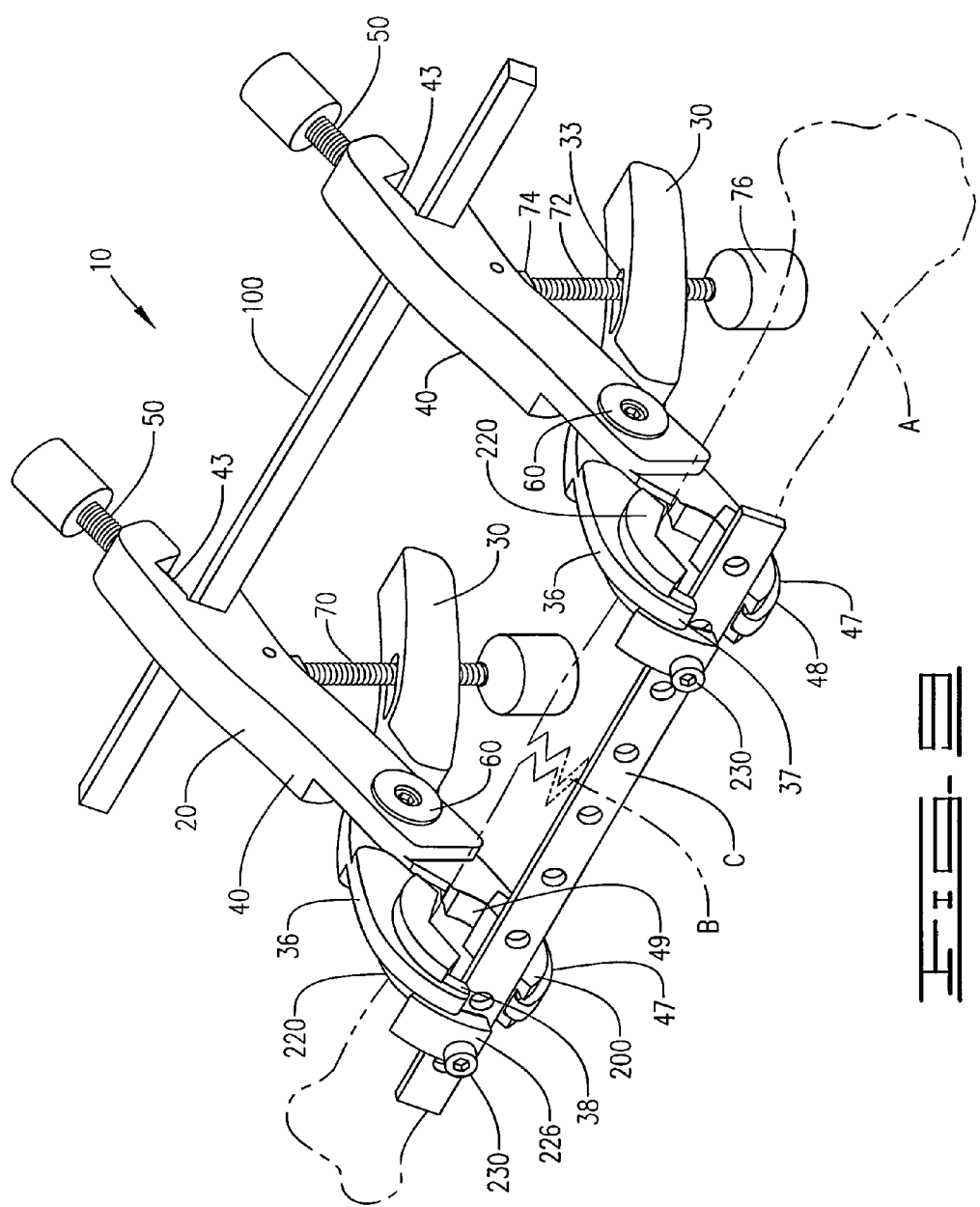

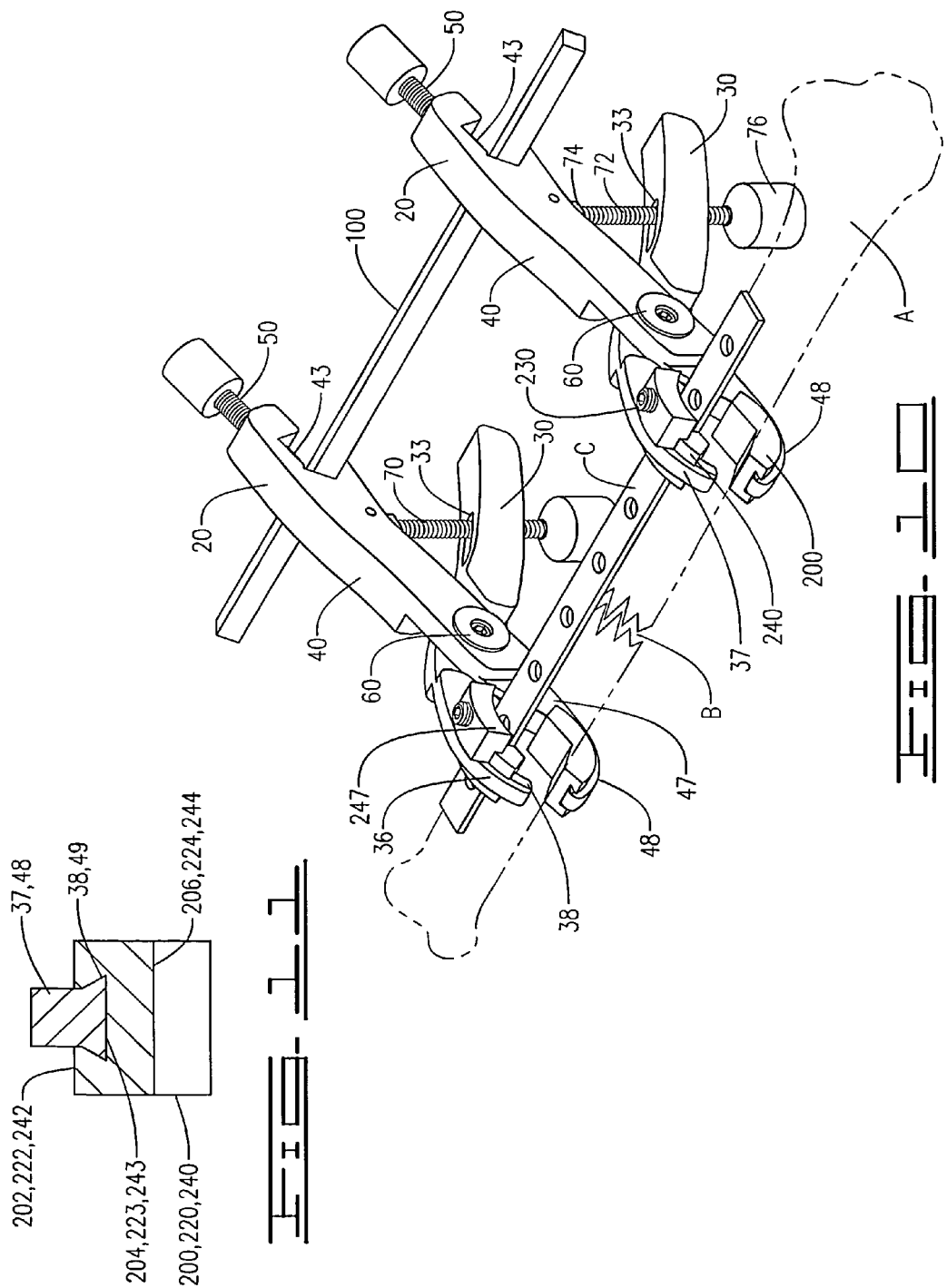

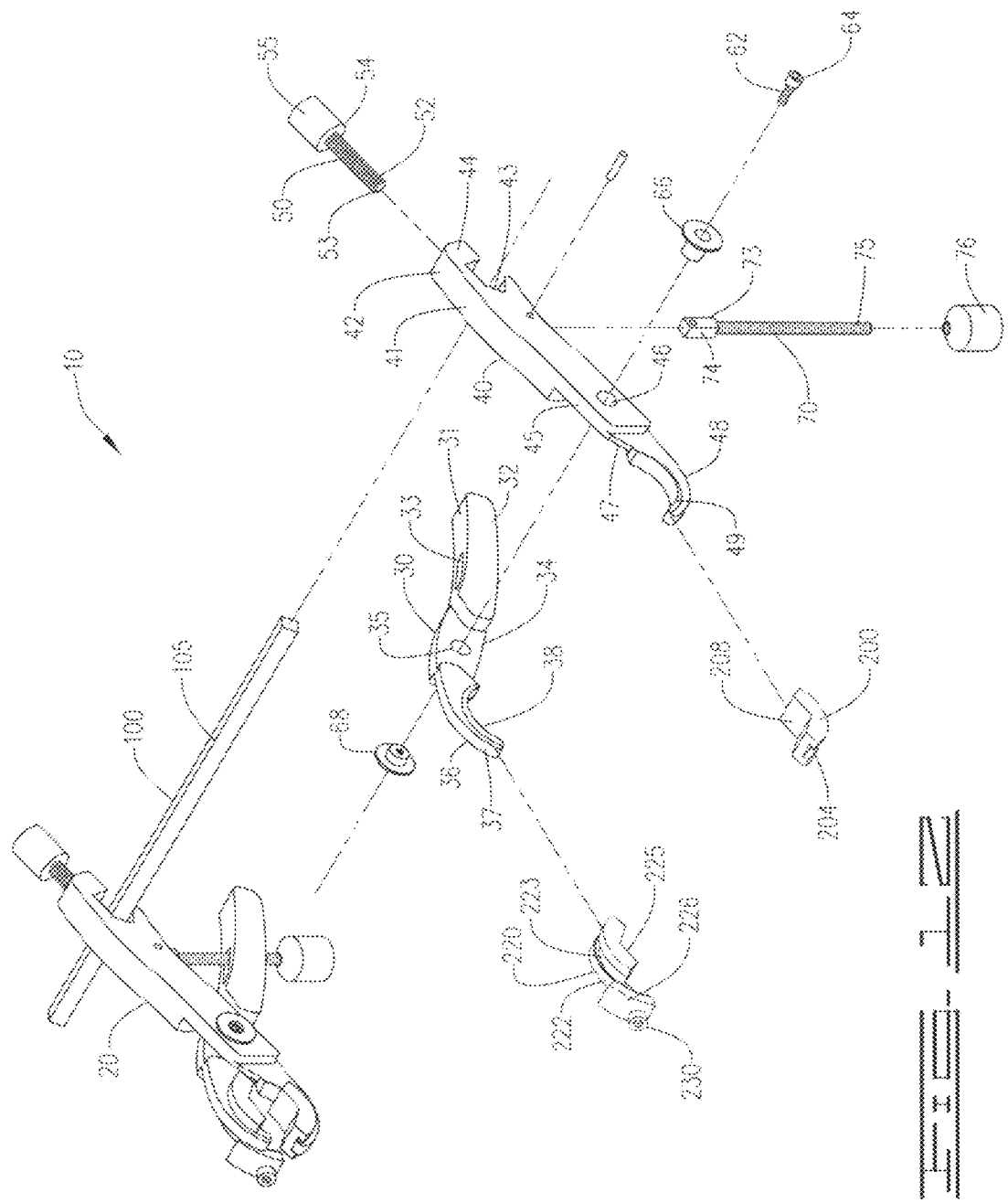

BONE REDUCTION AND PLATE CLAMP ASSEMBLY

CROSS REFERENCE TO RELATED APPLICATIONS

This is a Continuation-in-Part Application of U.S. patent application Ser. No. 12/655,005, filed on Dec. 22, 2009, by the same inventor.

I. BACKGROUND OF THE INVENTION

1. Field of Invention

A pair of clamps are attached to a damaged linear or non-linear bone one each side of a fracture site during a surgical reduction, one clamp on each side of the fracture site, after which the two clamps are slidably engaged to a pivotal alignment bar, with the clamps then being adjusted to properly align the linear or non-linear bone for a surgical attachment using a bone plate. The pivotal alignment bar provides at least one pivotal ball joint which may be aligned as a straight bar for a linear bone or adjusted to an angle for non-linear bones to achieve optimal alignment of the bone. Each clamp provides axially adjustable plate retainers which slides along a track on the end of each segment of the each clamp to position the retainers at a location where the bone plate is to be attached to the bone. Upon positioning, the bone plate is held against the bone with the bone still in proper alignment wherein screws anchor the plate to the bone, stabilizing the fracture site during the plate attachment procedure.

2. Description of Prior Art

A preliminary review of prior art patents was conducted by the applicant which reveal prior art patents in a similar field or having similar use. However, the prior art inventions do not disclose the same or similar elements as the present bone and plate clamp assembly, nor do they present the material components in a manner contemplated or anticipated in the prior art.

In a U.S. Patent Application, Publication No. 2008/0027471 to Hauri, a bone clamp is disclosed which provides a pair of members in a scissor engagement with and handle on one end and extended clamping jaws on the opposing ends, the extended clamping jaws having a plurality of sharp projecting teeth which clamp onto a bone segment, the jaws having a locking means to retain the jaws upon the bone. The handles also provide at least one point where the handle may be attached to an elongated component to fulfill a target line function in that the longitudinal axis of the component may be aligned in parallel with the load axis of the leg. In U.S. patent Application, Publication No. 2008/0009871 to Orbay, a bone clamp provides a C-shaped body with a lower V-shaped clamp plate having a serrated or ridged surface with an upper section forming an internally threaded aperture to receive a threaded screw attaching to a template having multiple holes serving as a guide for inserting of pins, screws or a drill member, the bone clamp also providing a detachable extended handle.

Bone clamps are also disclosed in the prior art which are used to clamp a segment of bone together to hold it in shape, where the bone has been severely splintered. These type clamps include U.S. Pat. No. 5,797,919 to Brinson, U.S. Pat. No. 3,477,429 to Sampson, and U.S. Pat. No. 2,427,128 to Ettinger. Some medical devices provide a means for reduction of a broken long bone for properly aligning the bone during a surgical repair. These type devices include U.S. Pat. No. 6,623,483 to Kazakov and U.S. Pat. No. 6,921,404 to Bimman.

A Bone plate clamp is disclosed in U.S. Pat. No. 4,187,840 to Watanabe, providing a base member with a guideway and an abutment face. A jaw member has a pair of jaw faces which face the abutment face, The jaw member is slidably mounted to the base member at the guideway and is movable toward and away from the abutment face by a leadscrew that is threaded to the base member, the jaw member defining a V-shaped clamping surface. The leadscrew has a grip with a first and second diameter to provide for different rates of movement of the jaw member. A bone setting apparatus is disclosed in U.S. Pat. No. 6,605,088 to St. Onge, providing a pair of bone clamps used for open reduction and internal fixation of a fractured bone or osteotomey, the bone clamps interconnected by a lockable articulating connection apparatus. Each bone clamp includes a primary clamping means for manipulating a bone fragment back into a proper position, Additionally, each bone clamp includes a secondary bone clamping means that provides adequate clamping force for maintaining the reduction so that the primary clamping means can be released. The secondary bone clamping means provides clearance for the positioning and application of a fracture fixation prosthesis to stabilize the reduction during healing. The bone clamps and lockable, articulating connection apparatus form a bone setting apparatus, with the bar engaged within each bone clamp.

None of the above disclosed sone clamps or alignment devices provide a means to secure two bone segments using a scissored clamping force with a locking means to retain the clamp into its clamped position, provide a secondary clamping means to secure each bone clamp to a common alignment bar which may be independently attached to each clamp prior to or subsequent to the clamps being secured to respective bone sections for subsequent linear alignment of the bones. None of the prior art devices provide the alignment bar with at least one pivotal ball joint which may be aligned as a straight bar for a linear bone or adjusted to an angle for non-linear bones to achieve optimal alignment of the bone. The prior art dos not provide a pair of bone plate securing members which secure to clamping ends of each bone clamp which may be adjustably axially aligned around the secured bone section forming opposing V-shaped clamping surfaces to minimize bone contact and still provide for secure contact with the bone section with positioned openings to allow for the insertion of a bone plate against a bone by yet another securing means, holding the bone plate in place while screws are inserted through the retained bone plate into the bone sections to hold the bone together and in place during the healing process and subsequent to the removal of the bone clamps.

II. SUMMARY OF THE INVENTION

Severely damaged displaced bone fractures which require surgical repair may be reduced and repaired using external fixation devices or in some instances, internal fixation devices which include the installation of bone plates. One such surgical procedure providing internal fixation of a broken bone is referred to as an osteotomy. In severe fractures of a bone, the bone may be broken into sections which will require alignment and then some type of securing means, including the application and installation of a bone plate using screws attaching the bone plate to each section of the broken bone across the fracture site.

The present device provides for a pair of bone clamps which are intended for two purposes—alignment and reduction of the bones and for holding the bone sections and bone plates in place during the internal fixation process. The paired bone clamps are attached to each section of the broken bone on opposing sides of the fracture site. Once the clamps are attached, they are secured to a common linear alignment bar at the handle end of each clamps independently while the clamp end of each clamp remains attached to its bone section. The clamps may be repositioned along the linear alignment bar to align the bone sections and move them together for the most optimal reduction. Once properly aligned, the clamps are them secured to the common alignment bar and left in place for the remainder of the surgical procedure. The clamps end provide clamping plates that may be axially adjusted along the clamping ends along a circular tracked guideway, each clamping plate defining a V-shaped clamping face with at least one sectional cutout per clamp defining a bone plate channel opening with a bone plate securing means, axially positional around each bone section and located at a position where the bone plate is to be attached across the fracture site to secure the bone sections together. The clamping plates may be moved during the surgical procedure to more than one position to allow for the installation of more than one bone plate at the same fracture site. Upon completion of the installation of the bone plate or bone plates, the clamps are removed and the surgical site is closed to allow the bone to heal and mend.

For non-linear bone alignment for reduction and repair, the alignment bar provides at least one pivotal ball joint which may be aligned as a straight bar for a linear bone or adjusted to an angle for non-linear bones to achieve optimal alignment of the bone. This pivotal application of the alignment bar provides the adjustment of the alignment bar to the optimal angle required for a non-linear bone, with the clamps then applied to a conforming bone plate to be secured upon the non-linear bone and then surgically secured to ensure proper alignment during the healing process of the non-linear bone.

The disclosed bone clamps and accessory assembly provide for a pair of clamps to be used to align and secure a broken bone for reduction and hold the broken bone in proper alignment and further provide for the secure placement of one or more bone plates across the fracture site being repaired. The clamps are provided with two clamp sections, each section defining a clamping end, and handle end and a central connection section where the two clamp sections are attached together in a pivotal scissor configuration with the clamping ends directed towards each other forming a clamp opening. The handle ends of each clamp are further attached to the linear alignment bar to hold each clamp attached to the bone in a position consistent with the proper alignment of the fractured bone. Each clamp end of each clamp section defines a semi-circular track flange, with the two clamp ends forming a circular tracked guideway, upon which at least one clamping plate is slidably engaged, each clamping plate providing a channel within which a bone plate may be secured against a bone section for subsequent attachment to the bone for repair of the fracture site.

III. DESCRIPTION OF THE DRAWINGS

The following drawings are submitted with this utility patent application.

FIG. 1 is a perspective view of one of the paired bone clamps.

FIG. 2 is a side view of one of the paired bone clamps.

FIG. 9 is an upper perspective view of the bone reduction and plate clamp assembly showing a pair of bone clamps attached to a fractured bone using adjustable clamp contact members and adjustable front projecting plate clamp members positioning a bone plate across the bone fracture site with the clamps further attaching to the common linear alignment bar.

FIG. 10 is an upper perspective view of the bone reduction and plate clamp assembly showing a pair of bone clamps attached to a fractured bone using adjustable clamp contact members and adjustable central plate clamp members positioning a bone plate across the bone fracture site with the clamps further attaching to the common linear alignment bar.

FIG. 11 is a cross sectional view along section lines 11/11 of FIG. 2.

FIG. 12 is a view of the bone reduction and plate clamp assembly indicating one bone clamp in an assembled embodiment and the other bone clamp in an exploded view, each bone clamp including an adjustable clamp contact member and an adjustable front projecting plate clamp member, with the bone clamp attached to the linear alignment bar, and indicating the attachment of the linear alignment bar with the alignment bar channel of the exploded bone clamp.

Figure 13:
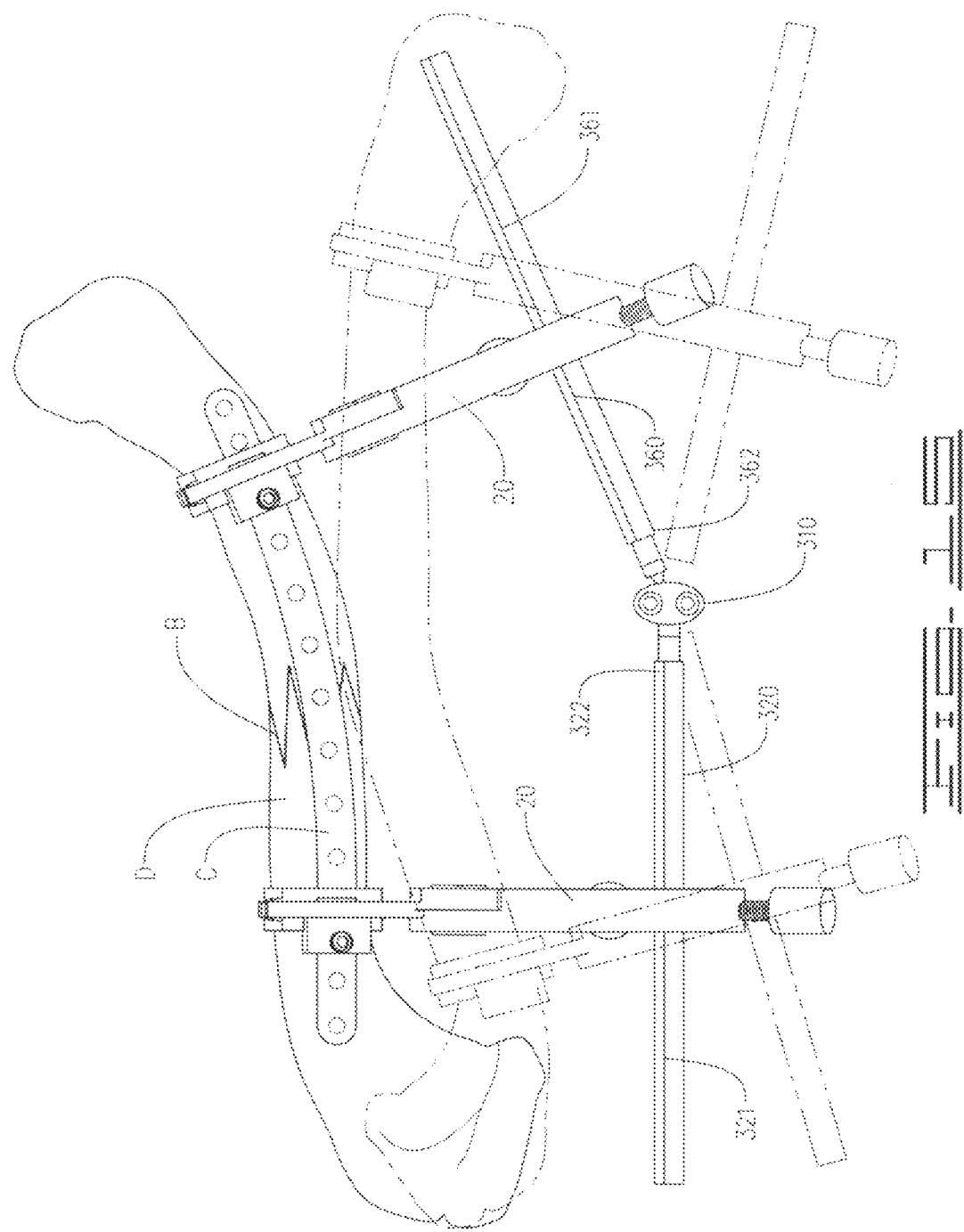

FIG. 13 is the pivotal alignment bar components in an exploded view.

Figure 14:
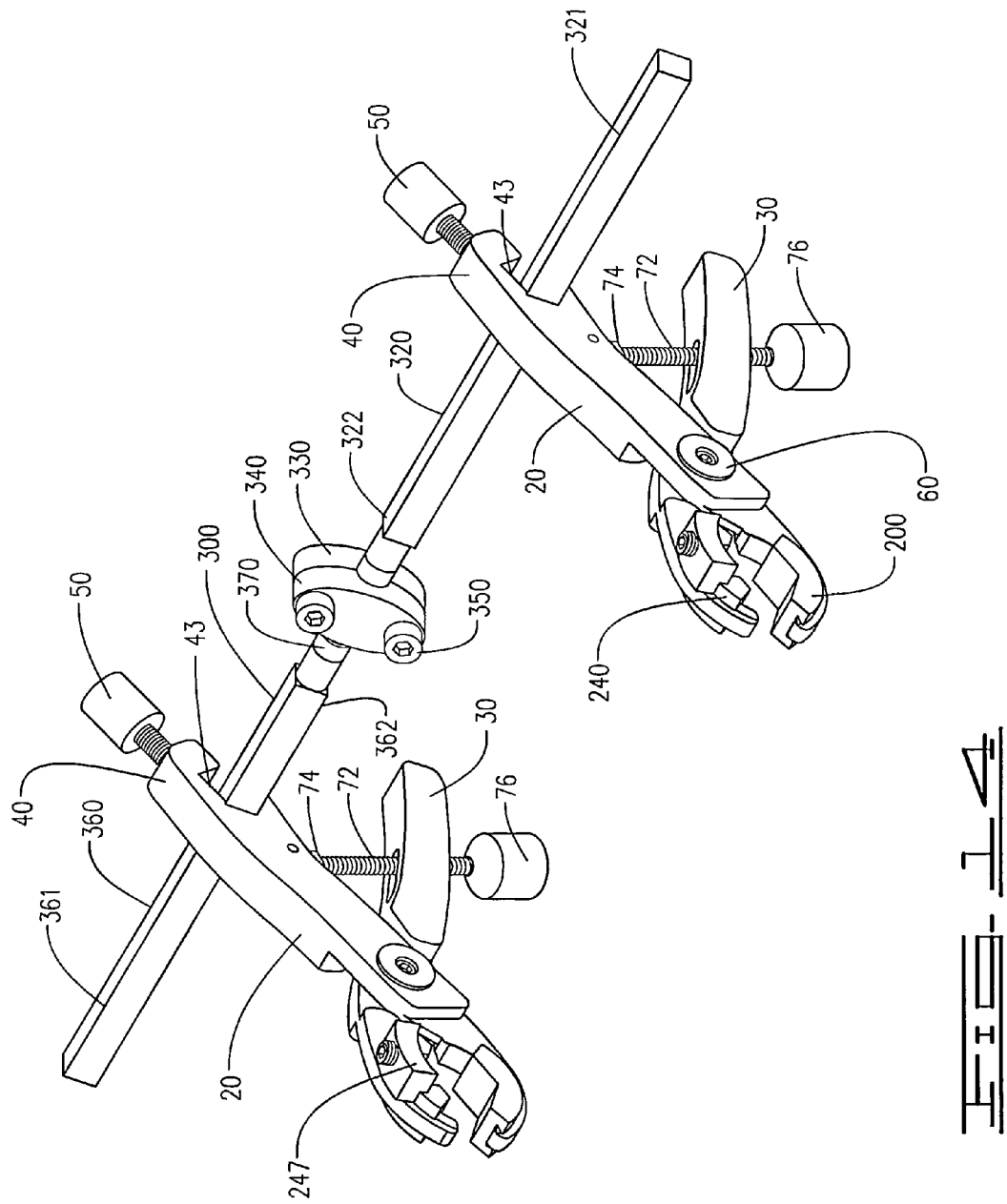

FIG. 14 is a perspective view of the bone reduction and plate clamp assembly using the pivotal alignment bar.

FIG. 15 is an upper perspective view of the bone reduction and plate clamp assembly showing a pair of bone clamps attached to a fractured non-linear bone using adjustable clamp contact members and adjustable front projecting plate clamp members positioning a bone plate across the bone fracture site with the clamps further attaching to the common pivotal alignment bar.

IV. DESCRIPTION OF THE PREFERRED EMBODIMENT

A bone reduction and plate clamp assembly 10 for the reduction of a fracture site B within a bone A and for the proper positioning and alignment of a bone plate C during the surgical repair of the bone, as shown and disclosed in FIGS. 1-12 of the drawings, provides a pair of bone clamps 20, a linear alignment bar 100, each bone clamp having at least two clamp members from a selection of at least one adjustable contact clamp member 200, at least one adjustable front projecting plate clamp member 220 or at least one adjustable central plate clamp member 240.

The linear alignment bar 100 is preferably a rigid bar having a square or other non-rounded profile, and would be a material that can withstand repeated use without deformation and also withstand repeated sterile cleansing for reuse. Most preferable of materials would be stainless steel, titanium or a non-porous plastic material. Using the square or non-rounded profile would reduce any potential rotation of the linear alignment bar over a rounded profile.

Each bone clamp 20 further comprises a scissor-like structure defining a first shaft member 30 and a second shaft member 40 which are hingedly and pivotally secured to each other through respective axial pivotal bores 35, 46 secured by a pivotal securing means 60. Each first shaft member 30 includes a first end 31 defining a handle 32, a central portion 34 defining the axial pivotal bore 35 and a second end 36 defining a semi-circular clamp end 37, each semi-circular clamp end 37 providing a flanged inner guideway 38. Each second shaft member 40 includes a first end 41 defining a handle 42, a shaped alignment bar retaining segment 43 conforming to the shape of the profile of the alignment bar 100, preferably square or other non-rounded profile, and an inner threaded sleeve 44 directed towards the retaining segment 43, a central portion 45 defining the axial pivotal bore 46 and a second end 47 defining a semi-circular clamp end 48, each semi-circular clamp end 48 providing a flanged inner guideway 49. The flanged inner guideways 38, 49 of the first and second shafts are identical in size shape and curvature. An outer threaded alignment bar pin 50 is threadably engaged within the inner threaded sleeve 44, defining a first end 52 providing a bar engagement tip 53 directed towards the retaining segment 43 to secure the linear alignment bar 100 within the retaining segment 43 and a second end 54 defining an expanded pin head 55. Having a square profile on the linear alignment bar 100 would further eliminate rotation or movement of the linear alignment bar 100 secured within the shaped alignment bar retaining segment 43, especially where the bar engagement tip 53 is directed against an edge 105 or a non-flat surface of the linear alignment bar 100, as indicated in FIG. 2.

The first shaft member 30 and second shaft member 40 are connected to each other through the respective axial pivotal bores 35, 46 by the pivotal securing means 60, shown in FIGS. 1, 2, 9, 10 and 12 as comprising an externally threaded bolt 62 having a bolt head 64, a recessed washer 66 receiving the bolt head 64 and an internally threaded flared nut 68, with the respective guideways 38, 49 of each semi-circular clamp end 37, 48 directed toward each other forming an overall circular opening to receive the bone, wherein an applied force upon each respective handle 32, 42 toward each other would cause the clamp ends 37, 48 to be forced towards one another and a force upon each handle 32, 42 away from each other would cause the clamp ends 37, 48 to be forced away from one another.

Each bone clamp 20 may further define a handle locking means 70, which is disclosed in FIGS. 1, 2, 9, 10 and 12 as including a threaded extension 72 defining a first end 73 having a shaped pivotal anchor head 74 pivotally attached within the handle 42 of the second shaft member 40 with a second end 75 directed through a vertical bore and extension slot 33 within the handle 32 of the first shaft 30 with an inner threaded locking nut 76 further secured to the second end 75 of the threaded extension 72 to lock the first and second shafts 30, 40 into a selected position.

Figure 3:
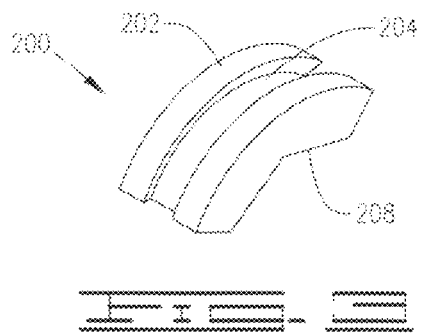
FIG. 3 is a lower perspective view of an adjustable clamp contact member.
Figure 4:
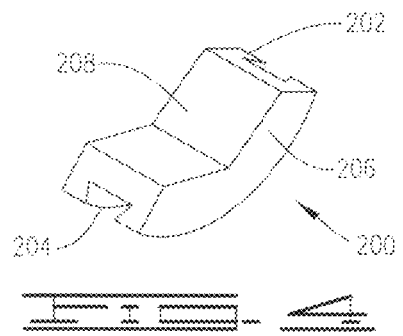
FIG. 4 is an upper perspective view of the adjustable clamp contact member.
Figure 5:
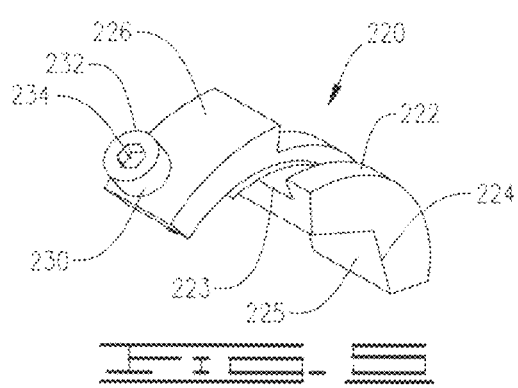
FIG. 5 is a lower perspective view of an adjustable front projecting plate clamp member.
Figure 6:
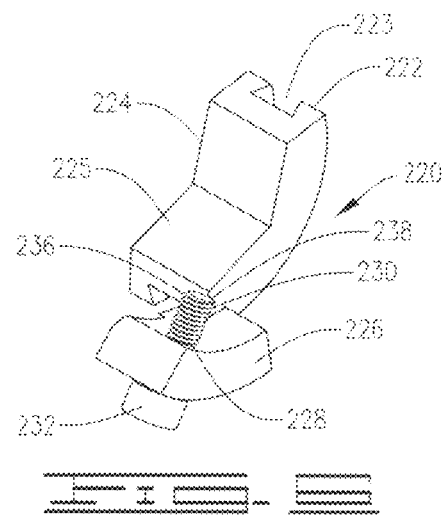
FIG. 6 is an upper perspective view of the adjustable front projecting plate clamp member.
Figure 7:
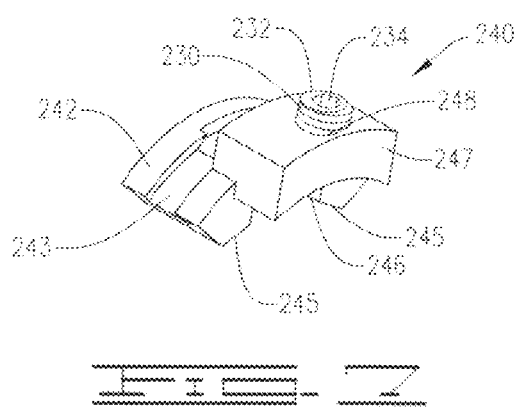
FIG. 7 is a lower perspective view of an adjustable central plate clamp member.
Figure 8:
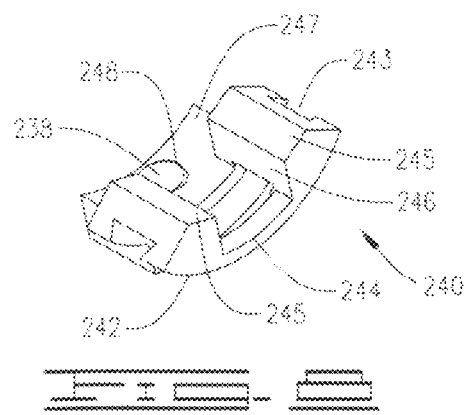
FIG. 8 is an upper perspective view of the adjustable central plate clamp member.
Figure 7:
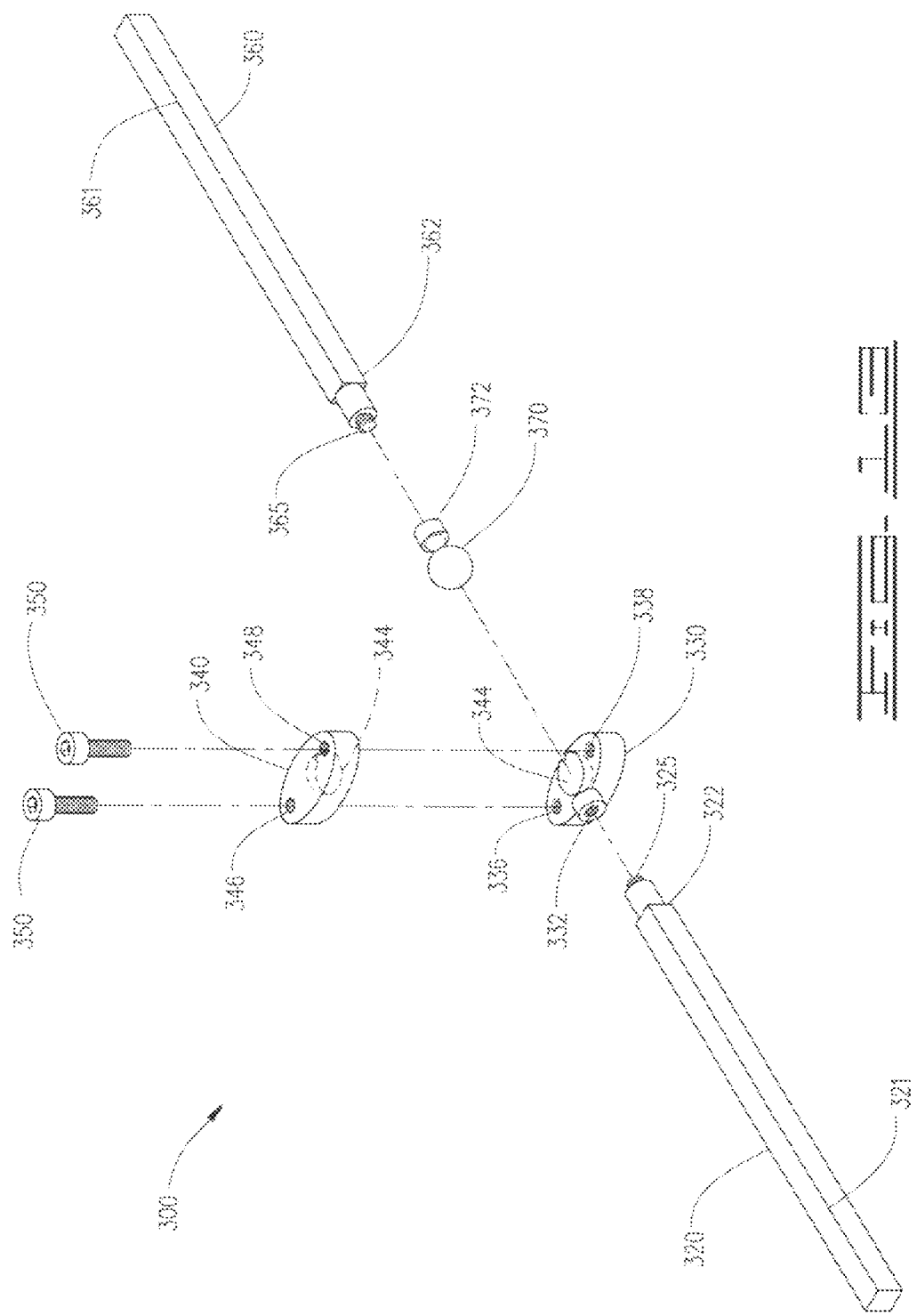

Each adjustable contact clamp member 200, as shown specifically in FIGS. 3 and 4, but also disclosed in all the other drawing figures, defines a rear surface 202 providing a dove-tailed semi-circular channel 204 slidable receiving the flanged inner guideway 38, 49 of the semi-circular shaped clamp end 37, 48 of the first or second shaft members 30, 40, similar to that indicated in FIG. 11. A front surface 206 of each adjustable contact clamp member 200 defines a V-shaped bone contact surface 208. Each adjustable front projecting plate clamp member 220, shown specifically in FIGS. 5 and 6, but also depicted in FIGS. 1-2, 9 and 12, defines a rear surface 222 providing a dove-tailed semi-circular channel 223 slidable receiving the flanged inner guideway 38, 49 of the semi-circular shaped clamp end 37, 48 of the first or second shaft member 30, 40, as indicated in FIG. 11.

A front surface 224 of each adjustable front projecting plate clamp member 220 defines a V-shaped bone contact surface 225 and an offset elevated plate clamp extension 226 having a vertical threaded bore 228 accepting an externally threaded set screw 230 having an upper end 232 defining a tool cavity 234 and a lower end 236 defining a plate contact tip 238. Each adjustable central plate clamp member 240, shown specifically in FIGS. 7 and 8, but also depicted in FIG. 10, defines a rear surface 242 providing a dove-tailed semi-circular channel 243 slidable receiving the flanged inner guideway 38, 49 of the semi-circular shaped clamp end 37, 48 of the first or second shaft member 30, 40, again similar to that indicated in FIG. 11. A front surface 244 of each adjustable central plate clamp member 240 defines two angled bone contact surfaces 245 on opposite sides of a plate clamp recess 246 extending a lateral elevated plate clamp extension 247 having a vertical threaded bore 248 accepting an externally threaded set screw 230 having an upper end 232 defining a tool cavity 234 and a lower end 236 defining a plate contact tip 238.

The surgeon employing the bone reduction and plate clamp assembly 10 may choose at their discretion the appropriate combination of clamp members during the surgical procedure most fitting for the placement and retention of at least one bone plate C over fracture site B of the bone A, and may choose to apply two bone plates at one time. With each clamp member being freely adjustable along the flanged inner guideway 38, 49 of each semi-circular clamp end 37, 48, the surgeon may adjust each clamp member to any position surrounding the bone, securing the clamp members in place against the bone A to which the bone clamp 20 is applied by squeezing the handles 32, 42 of the first and second shafts 30, 40 towards each other, with the handle locking means 70 retaining the first and second shaft 30, 40 together into a locked position.

The bone reduction and plate clamp assembly 10 may be utilized by a surgeon during an open reduction surgical procedure to set a broken bone into proper alignment and hold it in place for further internal fixation, to retain a bone plate during the internal fixation of the bone using screws and plates to enable or facilitate healing for rigid fixation to prevent micromotion across lines of fracture to enable healing and prevent infections, or to accomplish both tasks with one assembly. While most preferably utilized for the reduction of a long bone, including a femur, humerus, tibia, fibula, ulna, radius or collar bone, it is contemplated that this assembly 10 may be used with much smaller bones with the assembly 10 offered in a variety of sizes, depending upon what type of bone is being reduced, including small digits including a metatarsal, metacarpal or other small linear bones.

The reduction procedure utilizing the bone reduction and plate clamp assembly 10 would be performed after the injury site is opened and the broken bone with the soft tissue retracted to expose the fracture site and portions of the bone on each side. The each of the two bone clamps 20 upon which the selected clamp members have been applied and properly positioned along the flanged inner guideways 38, 49 of the semi-circular clamp ends 37, 48 would then be clamped to each bone portion on either side of the fracture site B utilizing the selected clamp members, most preferably at an equal distance from the fracture site B, with the two paired clamp members in firm contact with the bone portions. The handle locking means 70 is then secured to hold each bone clamp 20 in a firmly clamped position to each bone portion. Each bone portion would then be carefully manipulated using the bone clamps 20 until optimal alignment and reduction is accomplished. The linear alignment bar 100 would then be applied through the respective shaped alignment bar retaining segments 43 of each bone clamp 20 and affixed by rotating the expanded pin head 55 of each outer threaded alignment bar pin 50 until the linear alignment bar 100 is locked within both alignment bar retaining segments 43. This should retain the fractured bone in a proper alignment during the remainder of the open reduction surgical procedure with little or no movement, maintaining the fracture site is stable proximity for fixation.

At this point, the internal fixation may occur between the two secured bone clamps 20. If desired, the secured bone clamps 20 may further provide for the secure retention of the bone plate C over the fracture site B, depending upon which clamp members are used. As indicated in FIG. 10, where at least one adjustable central plate clamp member 240 and one contact clamp member 200 on each bone clamp 20 are applied, the bone plate C may be inserted underneath the lateral elevated plate clamp extension 247 of each clamp member and held against the bone A by rotating each externally threaded screw 230 forcing the plate contact tips 238 against the bone plate C and further against the bone A. Screws may then be inserted through the bone plate into the bone. This procedure may be repeated on different surfaces of the bone across the fracture site as many time as needed to fix the bone and hold it in place by simply releasing tension on each bone clamp 20 to some extent and rotating the clamp members around the flanged inner guideways 38, 49 of the first and second shaft members 30, 40 and even across the clamp ends 37, 48, shifting one clamp member from the flanged inner guideway 38 of the first shaft 30 to the flanged inner guideway 49 of the second shaft 40 without fully removing the bone clamp 20. This will reposition the central plate clamp member 240 to another section of the bone allowing for the application of a second bone plate across the fracture site on the bone.

As indicated in FIG. 9, where at least one adjustable front projecting plate clamp member 220 and one contact clamp member 200 per bone clamp are chosen, the bone plate C may be inserted underneath the offset elevated plate clamp extension 226 from the front of each clamp member and held against the bone A by rotating each externally threaded screw 230 forcing the plate contact tips 238 against the bone plate C and further against the bone A. Screws may then be inserted through the bone plate into the bone. This procedure may be repeated on different surfaces of the bone across the fracture site as many time as needed to fix the bone and hold it in place by simply releasing tension on each bone clamp 20 to some extent and rotating the clamp members around the flanged inner guideways 38, 49 of the first and second shaft members 30, 40 and even across the clamp ends 37, 48, shifting the clamp members from the flanged inner guideway 38 of the first shaft 30 to the flanged inner guideway 49 of the second shaft 40, or vise versa, without fully removing the bone clamp 20. This will reposition the front projecting plate clamp member 220 to another section of the bone allowing for the application of a second bone plate across the fracture site on the bone.

In another embodiment, the bone reduction and plate clamp assembly 10 for the reduction of a fracture site B within a non-linear bone D and for the proper positioning and alignment of a bone plate C during the surgical repair of the non-linear bone D, as shown and disclosed in FIGS. 1-8, 11 and 13-15 of the drawings, provides a pair of bone clamps 20, a pivotal alignment bar 300, each bone clamp having at least two clamp members from a selection of at least one adjustable contact clamp member 200, at least one adjustable front projecting plate clamp member 220 or at least one adjustable central plate clamp member 240. The bone clamps 20 are the same as indicated as previously disclosed. The pivotal alignment bar 300 is also preferably a rigid bar having an overall square or other non-rounded profile, and would be a material that can withstand repeated use without deformation and also withstand repeated sterile cleansing for reuse. Most preferable of materials would again be stainless steel, titanium or a non-porous plastic material. Having a square profile on the pivotal alignment bar 300 would further eliminate rotation or movement, just as the previously disclosed linear alignment bar 100, secured within the shaped alignment bar retaining segment 43, especially where the bar engagement tip 53 is directed against an edge 321, 361 or a non-flat surface of the pivotal alignment bar 300, as indicated in FIG. 14.

The pivotal alignment bar 300, FIG. 13, comprises a first bar section 320 having a first pivotal end 322 and a second bar section 360 having a second pivotal end 362, with the first and second pivotal ends 322, 362 defining at least one pivotal locking joint 310, allowing a locking angular positioning between the first bar section 320 and second bar section 360.

As indicated in a disclosed embodiment, FIGS. 13-15, the first pivotal end 322 defines an external thread 325 attached to an internally threaded cavity 332 of a pivotal joint plate base 330, the plate base 330 defining a rounded concavity 334 with a pair of outer flanges 336 with each outer flange providing an axially aligned threaded attaching aperture 338. A pivotal joint plate cap 340, FIG. 14, also defines a rounded concavity 344 and a pair of outer flanges 346, each outer flange 346 providing an axially aligned screw aperture 348, the outer flanges 336, 346 of the plate base 330 and plate cap 340 attached together by threaded screws 350 inserted through the screw apertures 348 of the plate cap 340 into the threaded screw apertures 338 of the plate base 340. The second pivotal end 362 of the second bar section 360, as indicated in FIG. 13, defines an external thread 365 attached within an internally threaded cavity 372 of a rounded pivotal joint ball member 370. To form the disclosed embodiment of the pivotal locking joint 310, the rounded pivotal joint ball member 370 is inserted between the plate base 330 and the plate cap 360 within the respective rounded concavities 334, 344, connecting the first and second bar sections 320, 360 together to form the pivotal alignment bar 300. By loosening the threaded screws 350, the rounded pivotal joint ball member 370 may be freely rotated between the plate base 330 and plate cap 340, without full disengagement, allowing the pivotal alignment bar 300 to be moved into a desired position angle. Once the desired position angle is obtained, the threaded screws 350 are tightened down, and the rounded pivotal ball member 370 is captured and maintained in a fixed position between the plate base 330 and plate cap 340. The bone clamps 20, may then be attached to the pivotal alignment bar 300 to stabilize the non-linear bone D for attachment of a bone plate C. It is contemplated that the pivotal alignment bar may be provided with more than one pivotal location.

Where the linear alignment bar 100 was intended for use in the reduction and fixation of a long bone, including a femur, humerus, tibia, fibula, ulna, radius, and in small embodiments, small digits including a metatarsal, metacarpal or other small linear bones, it is contemplated that the pivotal alignment bar 300 as part of the bone reduction and plate clamp assembly 10 may be used with non linear bones, including collar bones, FIGS. 14 and 15, scapulas, pelvis, and joint end attachments.

It is contemplated that in addition to those embodiments shown in the drawing figures, the surgeon may choose to utilize other combinations of clamp members including as many as four adjustable front projecting plate clamp members 220, four adjustable central plate clamp members 240, two adjustable front projecting plate clamp members 220 and two adjustable central plate clamp members 240 which would allow for the simultaneous securing of two bone plates across the fracture site on the bone. The selection of four adjustable contact clamp members 200 may also be utilized where the bone clamps 20 would only be used for the bone reduction procedure and not for the retention of bone plates.

While the bone reduction and plate clamp assembly has been particularly shown and described with reference to a preferred embodiment thereof, it will be understood by those skilled in the art that changes in form and detail may be made therein without departing from the spirit and scope of the intended function and use of the bone clamps and their respective components, the linear alignment bar or the different clamp members.

What is claimed is:

1. A bone reduction and plate clamp assembly used in the open reduction of a fracture site within a linear or non-linear bone and for the proper positioning and alignment of a bone plate during the surgical repair of the bone comprising:
   a pair of bone clamps, each bone clamp further comprising a scissor-like structure defining a first shaft member and a second shaft member hingedly and pivotally attached to each other through respective axial pivotal bores and secured by a pivotal securing means, said first shaft having a first end forming a handle, a central portion defining said axial pivotal bore and a second end providing a semi-circular clamp end, each said semi-circular clamp end providing a flanged inner guideway and said second shaft member having a first end forming a handle, a central portion defining said axial pivotal bore and a second end providing a semi-circular clamp end, each said semi-circular clamp end providing a flanged inner guideway, with said flanged inner guideways on each said semi-circular clamp end directed toward one another forming an overall circular opening;
   at least two of at least one adjustable contact clamp member, at least one adjustable front projecting plate clamp member, and at least one adjustable central plate clamp member, each contact member providing a rear surface defining a dove-tailed semi-circular channel slidably receiving said flanged inner guideway of each said flanged inner guideway of each said first and second shaft member; and
   a pivotal alignment bar including at least one pivotal locking joint between a first bar section and a second bar section each said bar section having a square or other non-rounded profile upon which to secure each said bone clamp at a desired and selected angle, a shaped alignment bar retaining segment conforming to a shape of a profile of said alignment bar, an inner threaded sleeve directed towards said alignment bar retaining segment, and an outer threaded alignment bar pin threadably engaged within said inner threaded sleeve, defining a first end providing a bar engagement tip direct towards said alignment bar retaining segment and a second end defining an expanded pin head, said expanded pin head rotated to drive said bar engagement tip into an edge of each said first or second bar section of said pivotal alignment bar, securing said first or second bar section of said pivotal alignment bar within said shaped alignment bar retaining segment without rotation of said first or second bar section of said pivotal alignment bar, wherein both said bone clamps are placed into proper and secure alignment upon bone on opposing sides of a fracture site during a bone reduction portion of a surgical procedure.

2. The bone reduction and plate clamp assembly, as disclosed in claim 1, each said bone clamp further comprising a handle locking means to lock said first and second shafts into a selected clamped position.

3. The bone reduction and plate clamp assembly, as disclosed in claim 1, wherein:
   each said adjustable contact clamp member further comprising a front surface defining a V-shaped bone contact surface;
   each said adjustable front projecting plate clamp member further comprising a front surface and an offset elevated plate clamp extension having a vertical threaded bore accepting an externally threaded set screw having an upper end extending above said elevated plate clamp extension and a lower end defining a plate contact tip; and
   each said adjustable central plate clamp member further comprising a front surface defining two angled bone contact surfaces on opposite sides of a plate clamp recess extending a lateral elevated plate clamp extension having a vertical threaded bore accepting an externally threaded set screw having an upper end extending above said lateral elevated plate clamp extension and a lower end defining a plate contact tip, each said set screw being rotatable to force each said plate contact tip below each said lateral elevated plate clamp extension or each said offset elevated plate clamp extension.

4. The bone reduction and plate clamp assembly, as disclosed in claim 1, each said at least one pivotal locking joint further comprising:
   a first bar section having a first pivotal end defining an external thread attaching within an internally threaded cavity of a pivotal joint plate base, said plate base defining a rounded concavity and a pair of outer flanges, each said outer flange providing an axially aligned threaded attaching aperture, a pivotal joint plate cap defining a rounded concavity and a pair of outer flanges, each said outer flange providing an axially aligned screw aperture, said outer flanges of said plate base and plate cap attaching together by threaded screws inserted through said screw apertures of said plate cap into said threaded screw apertures of said plate base; and
   a second bar section having a second pivotal end defining an external thread attaching within an internally threaded cavity of a rounded pivotal joint ball member, wherein said rounded pivotal joint ball member is inserted and kept between said plate base and said plate cap within said respective rounded concavities, connecting said first and second bar sections together to form said pivotal alignment bar and wherein by loosening said threaded screws, said rounded pivotal joint ball member is be freely rotated between said plate base and said plate cap, without full disengagement, allowing said pivotal alignment bar to be moved into a desired position angle after which said threaded screws are tightened down, capturing and holding said rounded pivotal ball member in a fixed and stationary position between said plate base and said plate cap.

5. A bone reduction and plate clamp assembly used in the open reduction of a fracture site within a linear or non-linear bone and for the proper positioning and alignment of a bone plate during the surgical repair of the linear or non-linear bone comprising:
   a pair of bone clamps, each bone clamp further comprising a scissor-like structure defining a first shaft member and a second shaft member hingedly and pivotally attached to each other through respective axial pivotal bores and secured by a pivotal securing means, said first shaft having a first end forming a handle, a central portion defining said axial pivotal bore and a second end providing a semi-circular clamp end, each said semi-circular clamp end providing a flanged inner guideway and said second shaft member having a first end forming a handle, a central portion defining said axial pivotal bore and a second end providing a semi-circular clamp end, each said semi-circular clamp end providing a flanged inner guideway, with said flanged inner guideways on each said semi-circular clamp end directed toward one another forming an overall circular opening;

a handle locking means to lock said first and second shafts into a selected clamped position;

at least two of at least one adjustable contact clamp member, at least one adjustable front projecting plate clamp member, and at least one adjustable central plate clamp member, each contact member providing a rear surface defining a dove-tailed semi-circular channel slidably receiving said flanged inner guideway of each said flanged inner guideway of each said first and second shaft member; and a pivotal alignment bar having at least one pivotal locking joint between a first bar section and a second bar section each said bar section having a square or other non-rounded profile upon which to secure each said bone clamp at a desired and selected angle, a shaped alignment bar retaining segment conforming to a shape of a profile of said alignment bar, an inner threaded sleeve directed towards said alignment bar retaining segment, and an outer threaded alignment bar pin threadably engaged within said inner threaded sleeve, defining a first end providing a bar engagement tip direct towards said alignment bar retaining segment and a second end defining an expanded pin head, said expanded pin head rotated to drive said bar engagement tip into an edge of each said first or second bar section of said pivotal alignment bar, securing said first or second bar section of said pivotal alignment bar within said shaped alignment bar retaining segment without rotation of said first or second bar section of said pivotal alignment bar, wherein both said bone clamps are placed into proper and secure alignment upon a bone on opposing sides of a fracture site during a bone reduction portion of a surgical procedure.

6. The bone reduction and plate clamp assembly, as disclosed in claim 5, wherein:

each said adjustable contact clamp member further comprising a front surface defining a V-shaped bone contact surface;

each said adjustable front projecting plate clamp member further comprising a front surface and an offset elevated plate clamp extension having a vertical threaded bore accepting an externally threaded set screw having an upper end extending above said elevated plate clamp extension and a lower end defining a plate contact tip; and each said adjustable central plate clamp member further comprising a front surface defining two angled bone contact surfaces on opposite sides of a plate clamp recess extending a lateral elevated plate clamp extension having a vertical threaded bore accepting an externally threaded set screw having an upper end extending above said lateral elevated plate clamp extension and a lower end defining a plate contact tip, each said set screw being rotatable to force each said plate contact tip below each said lateral elevated plate clamp extension or each said offset elevated plate clamp extension.

7. The bone reduction and plate clamp assembly, as disclosed in claim 5, said handle locking means further comprising a threaded extension defining a first end having a shaped pivotal anchor head pivotally attached within said handle of said second shaft member and a second end directed through a vertical bore and extension slot within said handle of said first shaft with an inner threaded locking nut further secured to said second end of said threaded extension to lock said first and second shafts into a selected position.

8. The bone reduction and plate clamp assembly, as disclosed in claim 5, said pivotal securing means further comprising an externally threaded bolt having a bolt head, a recessed washer receiving said bolt head and an internally threaded flared nut, said externally threaded bolt passed through said axial pivotal bores of said first and second shaft members with said internally threaded flared nut attached to said externally threaded bolt holding said first and second shaft members together in pivotal engagement.

9. The bone reduction and plate clamp assembly, as disclosed in claim 5, each said at least one pivotal locking joint further comprising:

a first bar section having a first pivotal end defining an external thread attaching within an internally threaded cavity of a pivotal joint plate base, said plate base defining a rounded concavity and a pair of outer flanges, each said outer flange providing an axially aligned threaded attaching aperture, a pivotal joint plate cap defining a rounded concavity and a pair of outer flanges, each said outer flange providing an axially aligned screw aperture, said outer flanges of said plate base and plate cap attaching together by threaded screws inserted through said screw apertures of said plate cap into said threaded screw apertures of said plate base; and a second bar section having a second pivotal end defining an external thread attaching within an internally threaded cavity of a rounded pivotal joint ball member, wherein said rounded pivotal joint ball member is inserted and kept between said plate base and said plate cap within said respective rounded concavities, connecting said first and second bar sections together to form said pivotal alignment bar and wherein by loosening said threaded screws, said rounded pivotal joint ball member is be freely rotated between said plate base and said plate cap, without full disengagement, allowing said pivotal alignment bar to be moved into a desired position angle after which said threaded screws are tightened down, capturing and holding said rounded pivotal ball member in a fixed and stationary position between said plate base and said plate cap.

10. A bone reduction and plate clamp assembly used in the open reduction of a fracture site within a linear or non-linear bone and for the proper positioning and alignment of a bone plate during the surgical repair of the linear or non-linear bone comprising:

a pair of bone clamps, each bone clamp further comprising a scissor-like structure defining a first shaft member and a second shaft member hingedly and pivotally attached to each other through respective axial pivotal bores and secured by a pivotal securing means, said first shaft having a first end forming a handle, a central portion defining said axial pivotal bore and a second end providing a semi-circular clamp end, each said semi-circular clamp end providing a flanged inner guideway and said second shaft member having a first end forming a handle, a central portion defining said axial pivotal bore and a second end providing a semi-circular clamp end, each said semi-circular clamp end providing a flanged inner guideway, with said flanged inner guideways on each said semi-circular clamp end directed toward one another forming an overall circular opening;

a handle locking means to lock said first and second shafts into a selected clamped position;

at least two of at least one adjustable contact clamp member, at least one adjustable front projecting plate clamp member, and at least one adjustable central plate clamp member, each contact member providing a rear surface defining a dove-tailed semi-circular channel slidably receiving said flanged inner guideway of each said flanged inner guideway of each said first and second shaft member; and a pivotal alignment bar defining a first bar section and a second bar section connected together by at least one pivotal locking joint, each said first and second bar section having a square or non-rounded profile secured between each said bone clamp, each said handle of each said second shaft member further comprising a shaped alignment bar retaining segment conforming to a shape of a profile of said pivotal alignment bar, an inner threaded sleeve directed towards said alignment bar retaining segment, and an outer threaded alignment bar pin threadably engaged within said inner threaded sleeve, defining a first end providing a bar engagement tip direct towards said alignment bar retaining segment and a second end defining an expanded pin head, wherein said expanded pin head is rotated driving said bar engagement tip into an edge of said respective first or second bar section of said pivotal alignment bar, securing said respective first or second bar section of said pivotal alignment bar within said shaped alignment bar retaining segment without rotation of said pivotal alignment bar, wherein both said bone clamps being placed on opposite sides of said fracture site securely maintain said bone in a stable position during a bone reduction portion of a surgical repair.

11. The bone reduction and plate clamp assembly, as disclosed in claim 10, wherein:

each said adjustable contact clamp member further comprising a front surface defining a V-shaped bone contact surface;

each said adjustable front projecting plate clamp member further comprising a front surface and an offset elevated plate clamp extension having a vertical threaded bore accepting an externally threaded set screw having an upper end extending above said elevated plate clamp extension and a lower end defining a plate contact tip, wherein a bone plate may be inserted below said offset elevated plate clamp extension with said set screw being rotatable to force said plate contact tip below said offset elevated plate clamp extension against said bone plate and against said bone; and each said adjustable central plate clamp member further comprising a front surface defining two angled bone contact surfaces on opposite sides of a plate clamp recess extending a lateral elevated plate clamp extension having a vertical threaded bore accepting an externally threaded set screw having an upper end extending above said lateral elevated plate clamp extension and a lower end defining a plate contact tip, wherein a bone plate may be inserted below said lateral elevated plate clamp extension and within said plate clamp recess, with said set screw being rotatable to force said plate contact tip below said lateral elevated plate clamp extension against said bone plate and against said bone.

12. The bone reduction and plate clamp assembly, as disclosed in claim 10, said handle locking means further comprising a threaded extension defining a first end having a shaped pivotal anchor head pivotally attached within said handle of said second shaft member and a second end directed through a vertical bore and extension slot within said handle of said first shaft with an inner threaded locking nut further secured to said second end of said threaded extension to lock said first and second shafts into a selected position.

13. The bone reduction and plate clamp assembly, as disclosed in claim 10, said pivotal securing means further comprising an externally threaded bolt having a bolt head, a recessed washer receiving said bolt head and an internally threaded flared nut, said externally threaded bolt passed through said axial pivotal bores of said first and second shaft members with said internally threaded flared nut attached to said externally threaded bolt holding said first and second shaft members together in pivotal engagement.

14. The bone reduction and plate clamp assembly, as disclosed in claim 10, each said at least one pivotal locking joint further comprising:

a first bar section having a first pivotal end defining an external thread attaching within an internally threaded cavity of a pivotal joint plate base, said plate base defining a rounded concavity and a pair of outer flanges, each said outer flange providing an axially aligned threaded attaching aperture, a pivotal joint plate cap defining a rounded concavity and a pair of outer flanges, each said outer flange providing an axially aligned screw aperture, said outer flanges of said plate base and plate cap attaching together by threaded screws inserted through said screw apertures of said plate cap into said threaded screw apertures of said plate base; and a second bar section having a second pivotal end defining an external thread attaching within an internally threaded cavity of a rounded pivotal joint ball member, wherein said rounded pivotal joint ball member is inserted and kept between said plate base and said plate cap within said respective rounded concavities, connecting said first and second bar sections together to form said pivotal alignment bar and wherein by loosening said threaded screws, said rounded pivotal joint ball member is be freely rotated between said plate base and said plate cap, without full disengagement, allowing said pivotal alignment bar to be moved into a desired position angle after which said threaded screws are tightened down, capturing and holding said rounded pivotal ball member in a fixed and stationary position between said plate base and said plate cap.

\* \* \* \* \*